(12) United States Patent
Morita et al.

(10) Patent No.: US 7,195,773 B2
(45) Date of Patent: Mar. 27, 2007

(54) PESTICIDAL COMPOSITION

(75) Inventors: Masayuki Morita, Shiga (JP); Mitsugu Iwasa, Shiga (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 463 days.

(21) Appl. No.: 10/399,394

(22) PCT Filed: Oct. 22, 2001

(86) PCT No.: PCT/JP01/09253

§ 371 (c)(1),
(2), (4) Date: Apr. 21, 2003

(87) PCT Pub. No.: WO02/34050

PCT Pub. Date: May 2, 2002

(65) Prior Publication Data

US 2004/0024026 A1    Feb. 5, 2004

(30) Foreign Application Priority Data

Oct. 23, 2000    (JP) .............................. 2000-322558

(51) Int. Cl.
| | |
|---|---|
| A01N 25/00 | (2006.01) |
| A61K 31/70 | (2006.01) |
| A61K 31/54 | (2006.01) |
| A61K 31/435 | (2006.01) |
| A61K 31/44 | (2006.01) |
| A61K 31/415 | (2006.01) |
| A61K 31/34 | (2006.01) |
| A61K 31/275 | (2006.01) |
| A61K 31/17 | (2006.01) |
| A01N 43/40 | (2006.01) |
| A01N 43/56 | (2006.01) |
| A01N 43/08 | (2006.01) |
| A01N 37/34 | (2006.01) |
| A01N 47/28 | (2006.01) |

(52) U.S. Cl. .......................... 424/405; 514/28; 514/30; 514/223.8; 514/277; 514/345; 514/351; 514/355; 514/407; 514/469; 514/521; 514/531; 514/594

(58) Field of Classification Search .................. 514/318, 514/330, 28, 30, 223.8, 277, 345, 351, 355, 514/407, 469, 521, 531, 594; 424/405; 546/193, 546/262, 265; 544/124
See application file for complete search history.

(56) References Cited

U.S. PATENT DOCUMENTS 5,360,806 A    11/1994    Toki et al.

FOREIGN PATENT DOCUMENTS

| DE | 199 39 395 | 4/2000 |
|---|---|---|
| EP | 0 580 374 | 1/1994 |
| HU | P9201236 | 10/1992 |
| HU | 210768 | 7/1995 |
| HU | 214898 | 10/1998 |
| JP | 01 034902 | 2/1989 |
| WO | 01 76369 | 10/2001 |
| WO | 02 05648 | 1/2002 |
| WO | WO 02/34050 | 5/2002 |

OTHER PUBLICATIONS

Database CA 'Online!, Chemical Abstracts Service, Columbus, OH, US retrieved from STN-International, accession No. 134:143251 CA XP002194664, 2000.
U.S. Appl. No. 10/504,158, filed Aug. 23, 2004, Morita et al.

*Primary Examiner*—John Pak
*Assistant Examiner*—Ernst Arnold
(74) *Attorney, Agent, or Firm*—Oblon, Spivak, McClelland, Maier & Neustadt, P.C.

(57) ABSTRACT

A pesticidal composition comprising a pesticidally effective amount of at least one of a pyridic compound of the formula (I) or it salt and at least one of other pesticides: wherein Y is a haloalkyl group, m is 0 or 1, and Q is or a substituted or unsubstituted heterocyclic group, (wherein X is an oxygen atom or a sulfur atom, $R^1$ and $R^2$ are respectively independently a hydrogen atom, a substituted or unsubstituted alkyl group, a substituted or unsubstituted alkenyl group, a substituted or unsubstituted alkynyl group, a substituted or unsubstituted cycloalkyl group, and the like.

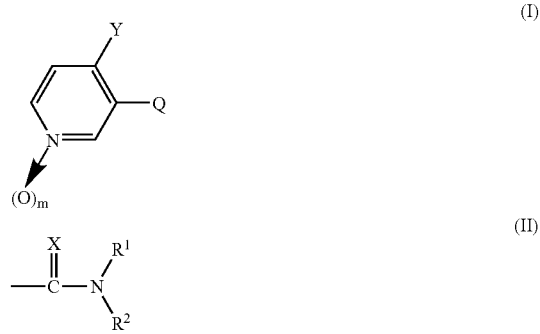

5 Claims, No Drawings

PESTICIDAL COMPOSITION

TECHNICAL FIELD

The present invention relates to an agriculturally useful pesticidal composition comprising a combination of a pyridic compound of the formula (I) described hereinafter or its salt with other insecticides, fungicides or the like.

BACKGROUND ART

Heretofore, an organophosphorus compound, a carbamate compound, a pyrethroid compound or the like has been used as an effective ingredient for an insecticide, but as this result, some insects have had a resistance to these insecticides in recent years. Therefore, it is demanded to provide an insecticide effective for these insects having a resistance. A pyridic compound of the formula (I) or its salt is disclosed in Japanese Patent No. 2994182, JP-A-10-195072, JP-A-11-180957, WO 98/57969, WO 00/35285, WO 00/35912, WO 00/35913, WO 01/9104, WO 01/14373 and the like.

Conventional pesticides have respectively characteristic spectrums and effects, but have some problems that the effects are sometimes unsatisfactory to certain pests, that their residual activities are sometimes poor and the effects are not satisfactorily maintained for a certain period of time, and that satisfactory pesticidal effects can not be practically achieved depending on applications. Also, even if there are some pesticides excellent in their pesticidal effects, they are demanded to be improved in respect of safety to fishes, crustacea and domestic animals and are also demanded to achieve a high pesticidal effect at a small dosage.

DISCLOSURE OF THE INVENTION

The present inventors have intensively studied to solve these problems, and as a result of the study, they have discovered that by combining a pyridic compound of the following formula (I) or its salt with other pesticide, unexpected effects of killing pests grown in some place by one time and reducing a dosage than in a case of using an effective component respectively alone, can be achieved. The present invention has been accomplished on the basis of this discovery.

That is, the present invention provides a pesticidal composition comprising at least one of a pyridic compound of the formula (I) or its salt and at least one of other pesticides:

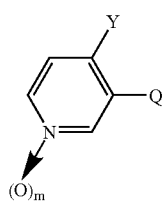

(I)

wherein Y is a haloalkyl group, m is 0 or 1, Q is

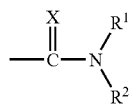

or a substituted or unsubstituted heterocyclic group, (wherein X is an oxygen atom or a sulfur atom, $R^1$ and $R^2$ are respectively independently a hydrogen atom, a substituted or unsubstituted alkyl group, a substituted or unsubstituted alkenyl group, a substituted or unsubstituted alkynyl group, a substituted or unsubstituted cycloalkyl group, a —$C(W^1)R^3$ group, a —$OR^4$ group, a —$S(O)_nR^5$ group, a —$NHR^6$ group,

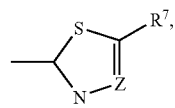

a —$C(R^8)$=NO—$R^9$ group or a substituted or unsubstituted aryl group, or $R^1$ and $R^2$ may form a =$C(R^{10})R^{11}$ group or may form a $C_4$–$C_5$ 5-membered or 6-membered heterocyclic group which may contain a nitrogen atom or an oxygen atom, together with an adjacent nitrogen atom, $R^3$ is a substituted or unsubstituted alkyl group, a substituted or unsubstituted alkenyl group, a substituted or unsubstituted alkynyl group, a substituted or unsubstituted cycloalkyl group, a substituted or unsubstituted aryl group, an alkoxy group, an alkylthio group or a mono- or dialkylamino group, $R^4$ is a hydrogen atom, a substituted or unsubstituted alkyl group, a substituted or unsubstituted alkenyl group, a substituted or unsubstituted alkynyl group, a substituted or unsubstituted cycloalkyl group, a substituted or unsubstituted aryl group, a substituted or unsubstituted heterocyclic group or a —$COR^3$ group, $R^5$ is an alkyl group or a dialkylamino group, $R^6$ is an alkyl group or an aryl group, Z is N or a —C—$R^7$ group, $R^7$ is a hydrogen atom, a halogen atom, a substituted or unsubstituted alkyl group, an alkoxy group, an alkylthio group or a nitro group, $R^8$ and $R^9$ are respectively independently a hydrogen atom, a substituted or unsubstituted alkyl group, a substituted or unsubstituted alkenyl group, a substituted or unsubstituted alkynyl group, a substituted or unsubstituted aryl group or a substituted or unsubstituted heterocyclic group, $R^{10}$ and $R^{11}$ are respectively independently a hydrogen atom, a substituted or unsubstituted alkyl group, a substituted or unsubstituted alkenyl group, a substituted or unsubstituted heterocyclic group, a —N—$(R^{12})R^{13}$ group, a substituted or unsubstituted alkoxy group, a substituted or unsubstituted alkylthio group, $R^{12}$ and $R^{13}$ are respectively independently a hydrogen atom, a substituted or unsubstituted alkyl group, a substituted or unsubstituted alkenyl group, a substituted or unsubstituted alkynyl group, a substituted or unsubstituted aryl group or a substituted or unsubstituted heterocyclic group, $W^1$ is an oxygen atom or a sulfur atom, and n is 1 or 2).

BEST MODE FOR CARRYING OUT THE INVENTION

In the above formula (I), Y includes a haloalkyl group such as $CF_3$, $CHF_2$, $CH_2F$, $CF_2Cl$, $CFCl_2$, $CCl_3$, $CH_2CF_3$, $CF_2CF_3$, $CHBr_2$, $CH_2Br$ or the like. Among them, a haloalkyl group having a carbon number of from 1 to 2 and a halogen atom of from 1 to 5 is preferable, and a trifluoromethyl group is particularly preferable.

In the formula (I), examples of a secondary substituent of a substituted or unsubstituted alkyl group defined as $R^1$, $R^2$, $R^3$, $R^4$, $R^7$, $R^8$, $R^9$, $R^{10}$, $R^{11}$, $R^{12}$ or $R^{13}$; a substituted or unsubstituted alkenyl group defined as $R^1$, $R^2$, $R^3$, $R^4$, $R^8$, $R^9$, $R^{10}$, $R^{11}$, $R^{12}$ or $R^{13}$; a substituted or unsubstituted alkynyl group defined as $R^1$, $R^2$, $R^3$, $R^4$, $R^8$, $R^9$, $R^{12}$ or $R^{13}$;

and a substituted or unsubstituted cycloalkyl group defined as $R^1$, $R^2$, $R^3$ or $R^4$ included in the group expressed by Q:

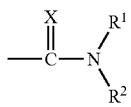

(hereinafter referred to as "$Q^1$ group"), include a halogen atom; an alkoxy group; an alkylthio group; a trialkylsilyl group; a phenyl group; a phenyl group substituted with a halogen, alkyl, alkoxy, nitro or haloalkyl group; a phenyl group substituted with a phenoxy group which may be substituted with an alkoxy or alkylthio group; a phenoxy group; a phenylthio group; an amino group; an amino group substituted with one or two alkyl group; a $C_{2-6}$ cyclic amino group; a morpholino group; a morpholino group substituted with an alkyl group; a 1-piperazinyl group; a 1-piperazinyl group substituted with an alkyl, phenyl, pyridyl or trifluoromethylpyridyl group; a heterocyclic group which may be substituted with a halogen, alkyl, alkoxy, haloalkoxy, alkylthio, phenyl (which may be further substituted with a halogen, alkyl, alkoxy, nitro, haloalkyl or phenoxy group), phenoxy, phenylthio, cycloalkyl or cycloalkoxy group; a hydroxy group; a cyano group; a cycloalkyl group; an imino group; a —C($W^2$)$R^{14}$ group ($W^2$ is an oxygen atom or a sulfur atom, $R^{14}$ is a hydrogen atom; an amino group; an amino group substituted with one or two alkyl group; an alkyl group; an alkoxy group; an alkylthio group or an aryl group); a —OC($W^2$)$R^{15}$ group ($R^{15}$ is an aryl group substituted with an alkyl or haloalkyl group); or an alkylsulfonyl group. Also, when the above substituent is an imino group, it may form an amidino group or an imidate group, together with an amino group or an alkoxy group.

Also, other examples of a substituent of a substituted or unsubstituted alkyl group defined as $R^1$ or $R^2$ included in the $Q^1$ group in the formula (I), include a 4-haloalkyl-3-pyridinecarboxyamide group, a N-methyl-4-haloalkyl-3-pyridinecarboxyamide group, a 4-haloalkyl-3-pyridinecarboxyamide-N-alkylenoxy group, and the like. A chemical structure formula of the formula (I) including these substituents is illustrated below:

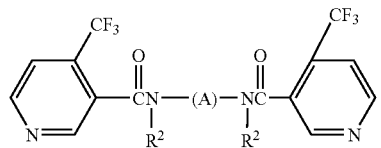

(wherein, $R^2$ is as defined above, A is a —(CH$_2$)$_1$— group or a —(CH$_2$)$_q$—O—(CH$_2$)$_q$— group, 1 is an integer of from 1 to 4 and q is 1 or 2).

Thus, the above compound is a dimer of a compound of the formula (I) connected by way of an alkylene chain. In the same manner as above, an effective component of the composition of the present invention includes a trimer.

Examples of a secondary substituent of a substituted or unsubstituted aryl group defined as $R^1$, $R^2$, $R^3$, $R^4$, $R^8$, $R^9$, $R^{12}$ or $R^{13}$ included in the $Q^1$ group in the formula (I), include a halogen atom; an alkyl group; a haloalkyl group; an alkoxy group; a haloalkoxy group; an alkylthio group; a cycloalkyl group; a cycloalkoxy group; an alkoxycarbonyl group; an alkylcarbonyl group; an alkylcarbonyloxy group; an aryl group; an aryloxy group; an arylthio group; an amino group; an amino group substituted with 1 or 2 alkyl group; a cyano group; a nitro group; a hydroxy group; and the like.

Examples of a secondary substituent of a substituted or unsubstituted heterocyclic group defined as $R^4$, $R^8$, $R^9$, $R^{10}$, $R^{11}$, $R^{12}$ or $R^{13}$ included in the $Q^1$ group in the formula (I), include a halogen atom; an alkyl group; an alkoxy group; a haloalkoxy group; an alkylthio group; a phenyl group which may be substituted with a halogen, alkyl, alkoxy, nitro, haloalkyl or phenoxy group; a phenoxy group; a phenylthio group; a cycloalkyl group; a cycloalkoxy group; and the like.

Examples of an alkyl moiety or an alkyl group included in the $Q^1$ group in the formula (I) include a group having a carbon number of from 1 to 6 such as a methyl group, an ethyl group, a propyl group, a butyl group, a pentyl group, a hexyl group and the like, and a group having a carbon number of at least 3 may include a linear or branched chain structure isomer. Examples of an alkenyl group included in the $Q^1$ group in the formula (I) include a group having a carbon number of from 2 to 6 such as an ethenyl group, a propylenyl group, a butenyl group, a pentenyl group, a hexenyl group and the like, and a group having a carbon number of at least 3 may include a linear or branched chain structure isomer. Examples of an alkynyl group included in the $Q^1$ group in the formula (I) include a group having a carbon number of from 2 to 6 such as an ethynyl group, a propynyl group, a butynyl group, a pentynyl group, a hexynyl group, and a group having a carbon number of at least 4 may include a linear of branched chain structure isomer. Examples of a cycloalkyl group included in the $Q^1$ group in the formula (I) include a group having a carbon number of from 3 to 8 such as a cyclopropyl group, a cyclobutyl group, a cyclopentyl group or a cyclohexyl group.

Examples of a $C_4$–$C_5$ 5-membered or 6-membered heterocyclic group which may contain a nitrogen atom or an oxygen atom, formed from $R^1$ and $R^2$ together with an adjacent nitrogen atom, included in the $Q^1$ group in the formula (I), include a morpholino group, a pyrrolidino group, a piperidino group, a 1-imidazolidinyl group, a 2-cyanoimino-3-methyl-1-imidazolidinyl group, a 1-piperazinyl group or a 4-methyl-1-piperazinyl group.

Examples of an aryl group included in the $Q^1$ group in the formula (I) include a phenyl group, a thienyl group, a furanyl group, a pyridyl group, a naphthyl group, a benzothienyl group, a benzofuranyl group, a quinolinyl group and the like.

Examples of a heterocyclic moiety of a substituted or unsubstituted heterocyclic group included in the $Q^1$ group in the formula (I) include a 5 to 7-membered monocyclic or phenyl-condensed cyclic group containing 1 to 3 hetero atoms selected from a nitrogen atom, an oxygen atom and a sulfur atom, such as a pyridyl group, a thienyl group, a furyl group, a pirazinyl group, a pyrimidinyl group, a tetrahydrofuranyl group, a thiazolyl group, an isooxazolyl group, a quinolyl group, a pyrazolyl group, an oxazolyl group, an oxadiazolyl group, a thiadiazolyl group, a triazolyl group and the like.

Examples of a heterocyclic moiety of a substituted or unsubstituted heterocyclic group represented by Q in the formula (I) include preferably a 5 to 7-membered monocyclic group containing 2 to 3 hetero atoms selected from a nitrogen atom, an oxygen atom and a sulfur atom, such as a 5-membered monocyclic group including a pyrazolyl group, an oxazolyl group, a thiazolyl group, an oxydiazolyl group, a thiadiazolyl group, a triazolyl group and the like; and a 6-membered monocyclic group such as:

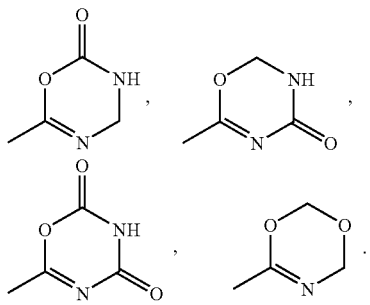

Examples of a secondary substituent of a substituted or unsubstituted heterocyclic group expressed by Q in the formula (I) include a halogen atom, a nitro group, a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted cycloalkyl group, a hydroxyl group, a substituted or unsubstituted alkoxy group, a substituted or unsubstituted alkenyloxy group, a substituted or unsubstituted alkynyloxy group, a substituted or unsubstituted aryloxy group, a substituted or unsubstituted heterocyclicoxy group, a substituted or unsubstituted cycloalkoxy group, a mercapto group, a substituted or unsubstituted alkylthio group, a substituted or unsubstituted arylthio group, a substituted or unsubstituted alkenylthio group, a substituted or unsubstituted alkynylthio group, a substituted or unsubstituted arylthio group, a substituted or unsubstituted heterocyclicthio group, a substituted or unsubstituted cycloalkylthio group, a substituted or unsubstituted carbonyl group, a substituted or unsubstituted alkoxycarbonyl group, a substituted or unsubstituted arylcarbonyl group, a substituted or unsubstituted carbonyloxy group, a formyl group, a substituted or unsubstituted ester group, a substituted or unsubstituted acyl group, a substituted or unsubstituted sulfonyl group, a substituted or unsubstituted sulfyl group, a substituted or unsubstituted sulfonyloxy group, a substituted or unsubstituted alkylsulfyl group, a substituted or unsubstituted sulfonylalkyl group, a substituted or unsubstituted amino group, a substituted or unsubstituted isocyanate group, a substituted or unsubstituted arylalkyl group, a substituted or unsubstituted heterocyclic alkyl group, and the like.

Among these secondary substituents, some substituents may further be substituted with a tertiary substituent such as a halogen atom; a cyano group; an alkyl group which may be substituted with halogen, haloalkyl, cyano, alkoxy or aryl; an alkoxy group which may be substituted with halogen or aryl; a hydroxyl group; an amino group which may be substituted with alkylsulfonyl, arylalkyl, heterocyclic alkyl, alkyl, aryl, alkylaryl, alkylhydroxy, cyanoalkyl, alkynyl, alkenyl or cycloalkyl; a carbonyl group which may be substituted with alkoxy, alkylamino or alkyl; an alkylthio group; an aryloxy group; an arylthio group; an aryl group which may be substituted with halogen, haloalkoxy, alkyl or aryl; a nitro group; an arylcarbonyloxy group which may be substituted with halogen or nitro; a cycloalkyl group; an alkylsulfonyloxy group; an alkylcarbonyloxy group; an isocyanate group which may be substituted with alkyl, haloalkyl, alkenyl, alkynyl, heterocyclic alkyl, aryloxy, aryloxyalkyl, alkoxy, alkoxycarbonylalkyl, hydroxyalkyl, cyanoalkyl, alkoxyalkyl, alkenyl, arylalkoxy or alkoxycarbonylalkyl; an arylalkylisocyanate group which may be substituted with arylalkyl, halogen, alkyl or alkoxy; a cycloalkylcarbonyloxy group; a cycloalkylisocyanate group which may be substituted with haloalkyl; an alkynylalkylisocyanate group; an arylisocyanate group which may be substituted with alkyl, alkoxy, alkylthio, halogen, hydroxyl group, haloalkoxy, nitro, halogen-substituted aryloxy or aryloxy; a heterocyclic group which may be substituted with alkyl, alkoxy, aryl or ester; an alkoxyisocyano group; and the like.

Examples of an alkyl moiety or an alkyl group in a secondary substituent or a tertiary substituent of a substituted or unsubstituted heterocyclic group expressed by Q in the formula (I), include a group having a carbon number of from 1 to 6, such as a methyl group, an ethyl group, a propyl group, a butyl group, a pentyl group or a hexyl group, and a group having at least 3 carbon atoms may be a linear or branched chain structure isomer. Examples of an alkenyl group include a group having a carbon number of from 2 to 6, such as an ethenyl group, a propenyl group, a butenyl group, a pentenyl group or a hexenyl group, and a group having at least 3 carbon atoms may be a linear or branched chain structure isomer. Examples of an alkynyl group include a group having a carbon number of from 2 to 6, such as an ethynyl group, a propinyl group, a butynyl group, a pentynyl group or a hexynyl group, and a group having at least 3 carbon atoms may be a linear or branched chain structure isomer. Examples of a cycloalkyl group include a group having a carbon number of from 3 to 8, such as a cyclopropyl group, a cyclobutyl group, a cyclopentyl group or a cyclohexyl group. Examples of an aryl group include a phenyl group, a thienyl group, a furanyl group, a pyridyl group, a naphthyl group, a benzothienyl group, a benzofuranyl group or a quinolinyl group. Examples of a heterocyclic group include a 5-membered or 6-membered monocyclic or phenyl-condensed cyclic group having 1 to 3 hetero atoms selected from a nitrogen atom, an oxygen atom and a sulfur atom, such as a pyridyl group, a thienyl group, a furyl group, a pyrazinyl group, a thiazolyl group, an isooxazolyl group and a quinolyl group.

A compound of the formula (I) may form a salt with an acidic material or a basic material, and examples of a salt with an acidic material include an inorganic acid salt such as a hydrochloride, a hydrobromide, a phosphate, a sulfate or a nitrate, and examples of a salt with a basic material include an inorganic or organic base salt such as a sodium salt, a potassium salt, a calcium salt, an ammonium salt or a dimethylamine salt.

A compound of the formula (I) or its salt can be produced in accordance with a method disclosed in Japanese Patent No. 2994182, JP-A-10-195072, JP-A-11-180957, WO 98/57969, WO 00/35285, WO 00/35912, WO 00/35913, WO 01/9104, WO 01/14373 or the like.

Examples of a pyridic compound or its salt preferable as an effective component of a pesticidal composition of the present invention are illustrated below, but the present invention is not limited thereto.

(1) A pyridic compound expressed by the following formula (I) or its salt:

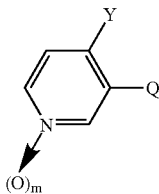
(I)

wherein Y, m and Q are as defined above.

(2) A compound of the above formula (I) or its salt, wherein Q is:

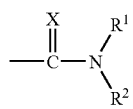

wherein X is an oxygen atom or a sulfur atom, $R^1$ and $R^2$ are respectively independently a hydrogen atom, a substituted or unsubstituted alkyl group, a substituted or unsubstituted alkenyl group, a substituted or unsubstituted alkynyl group, a substituted or unsubstituted cycloalkyl group, a —C($W^1$)$R^3$ group, a —S(O)$_n$$R^5$ group, a —NH$R^6$ group,

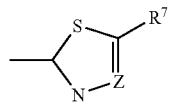

or a —C($R^8$)=NO—$R^9$ group, or $R^1$ and $R^2$ may form a =C($R^{10}$)$R^{11}$ group or may form a $C_4$–$C_5$ 5-membered or 6-membered heterocyclic group which may contain a nitrogen atom or an oxygen atom, together with an adjacent nitrogen atom, and $R^3$, $R^5$, $R^6$, Z, $R^7$, $R^8$, $R^9$, $R^{10}$, $R^{11}$, $W^1$ and n are as defined above.

(3) A compound of the above formula (I) or its salt, wherein Q is:

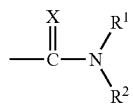

(wherein X is an oxygen atom or a sulfur atom, $R^1$ and $R^2$ are respectively independently a hydrogen atom, a substituted or unsubstituted alkyl group, a substituted or unsubstituted alkenyl group, a substituted or unsubstituted alkynyl group, a substituted or unsubstituted cycloalkyl group, a —C($W^1$)$R^3$ group, a —S(O)$_n$$R^5$ group or a —NH$R^6$ group, or $R^1$ and $R^2$ may form a =C($R^{10}$)$R^{11}$ group or may form a $C_4$–$C_5$ 5-membered or 6-membered heterocyclic group which may contain a nitrogen atom or an oxygen atom, together with an adjacent nitrogen atom, and $R^3$, $R^5$, $R^6$, $W^1$ and n are as defined above, and $R^{10}$ and $R^{11}$ are respectively independently an alkoxy group or an alkylthio group.

(4) A compound of the above formula (I) or its salt, wherein Q is:

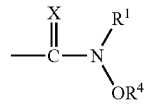

wherein X is an oxygen atom or a sulfur atom, $R^1$ is a hydrogen atom, a substituted or unsubstituted alkyl group, a substituted or unsubstituted alkenyl group, a substituted or unsubstituted alkynyl group, a substituted or unsubstituted cycloalkyl group, a substituted or unsubstituted aryl group or a —C($W^1$)$R^3$ group, and $R^3$, $R^4$ and $W^1$ are as defined above.

(5) A compound or its salt of the above (2) or (3), wherein X is an oxygen atom.

(6) A compound of the above (3) or its salt, wherein $R^1$ and $R^2$ are respectively independently a hydrogen atom, a substituted or unsubstituted alkyl group or a —C($W^1$)$R^3$ group, or $R^1$ and $R^2$ may form a =C($R^{10}$)$R^{11}$ group, $W^1$ is an oxygen atom or a sulfur atom, $R^3$ is a substituted or unsubstituted alkyl group, a substituted or unsubstituted aryl group or an alkoxy group, and $R^{10}$ and $R^{11}$ are respectively independently an alkoxy group or an alkylthio group.

(7) A compound or its salt of the above (2), wherein $R^1$ is a hydrogen atom, $R^2$ is a —C($R^8$)=NO—$R^9$ group, and $R^8$ and $R^9$ are as defined above.

(8) A compound or its salt of the above (2), wherein $R^1$ and $R^2$ or m a =C($R^{10}$)—N($R^{12}$)$R^{13}$ group, and $R^{10}$ is a hydrogen atom, a substituted or unsubstituted alkyl group, a substituted or unsubstituted alkenyl group or a substituted or unsubstituted heterocyclic group, and $R^{12}$ and $R^{13}$ are as defined above.

(9) A compound or its salt of the above (2), wherein $R^1$ is a hydrogen atom, and $R^2$ is

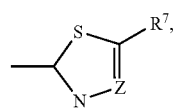

(wherein Z an $R^7$ are as defined above).

(10) A compound or its salt of the above (3), wherein X is an oxygen atom, $R^1$ and $R^2$ are respectively independently a hydrogen atom, an alkyl group, an alkoxyalkyl group, an alkylaminoalkyl group, a $C_{2-6}$ cyclic aminoalkyl group, a hydroxyalkyl group, a cyanoalkyl group, a thiocarbamoylalkyl group, an alkylcarbonyloxyalkyl group, an alkylcarbonyl group, an arylcarbonyl group, a trifluoromethyl-substituted arylcarbonyl group, an alkoxythiocarbonyl group or an alkoxycarbonyl group, or $R^1$ and $R^2$ may form a =C($R^{10}$)$R^{11}$ group, and $R^{10}$ and $R^{11}$ are respectively an alkoxy group and an alkylthio group.

(11) A compound or its salt of the above (1), wherein the compound of the formula (I) is at least one member selected from the group consisting of N-cyanomethyl-4-trifluoromethyl-3-pyridinecarboxyamide (Compound No. 1), N-ethyl-4-trifluoromethyl-3-pyridinecarboxyamide (Compound No. 2), 4-trifluoromethyl-3-pyridinecarboxyamide 1-oxide (Compound No. 3), 4-trifluoromethyl-3-pyridinecarboxyamide (Compound No. 4), N-thiocarbamoylmethyl-4-trifluoromethyl-3-pyridinecarboxyamide, N-ethoxymethyl-4-trifluoromethyl-3-pyridinecarboxyamide, N-isopropylaminomethyl-4-trifluoromethyl-3-pyridinecarboxyamide, N-cyanomethyl-N,N-bis(4-trifluoromethylnicotinoyl)amine, N-acetyl-N-cyanomethyl-4-trifluoromethyl-3-pyridinecarboxyamide, N-cyanomethyl-N-methyl-4-trifluoromethylpyridine-3-carboxyamide, O-methyl N-(4-trifluoromethylnicotinoyl)thiocarbamate, N-methyl-4-trifluoromethylpyridine-3-carboxyamide, N-(N',N'-diemthylaminomethyl)-4-trifluoromethylpyridine-3-carboxyamide, N-(1-piperidylmethyl)-4-trifluoromethylpyridine-3-carboxyamide, N-cyanomethyl N-(4-trifluoromethylnicotinoyl)aminomethylpivalate, O,S-dimethyl N-(4-trifluoromethylnicotinoyl)iminoformate, N-hydroxymethyl-4-trifluoromethyl-3-pyridinecarboxyamide, N-acetyl-4-trifluoromethyl-3-pyridinecarboxyamide and methyl N-(4-trifluoromethylnicotinoyl)carbamate or their 1-oxides.

(12) A compound or its salt of the above (1), wherein a compound of the formula (I) is at least one member selected from the group consisting of N-cyanomethyl-4-trifluoromethyl-3-pyridinecarboxyamide, N-ethyl-4-trifluoromethyl-3-pyridinecarboxyamide, 4-trifluoromethyl-3-pyridinecarboxyamide 1-oxide and 4-trifluoromethyl-3-pyridinecarboxyamide.

(13) A compound or its salt of the above (1), wherein a compound of the formula (I) is N-cyanomethyl-4-trifluoromethyl-3-pyridinecarboxyamide and/or 4-trifluoromethyl-3-pyridinecarboxyamide.

(14) A compound or its salt of the above (1), wherein a compound of the formula (I) is N-cyanomethyl-4-trirfluoromethyl-3-pyridinecarboxyamide.

(15) A compound or its salt of the above (1), wherein a compound of the formula (I) is 4-trifluoromethyl-3-pyridinecarboxyamide.

(16) A compound or its salt of the above (1), wherein Q is a substituted or unsubstituted heterocyclic group.

(17) A compound or its salt of the above (16), wherein the heterocyclic group moiety is a 5 to 7-membered monocyclic group having 2 to 3 hetero atoms selected from the group consisting of a nitrogen atom, an oxygen atom and a sulfur atom.

(18) A compound or its salt of the above (16), wherein the heterocyclic group moiety is a 5-membered monocyclic group containing 2 to 3 hetero atoms selected from the group consisting of a nitrogen atom, an oxygen atom and a sulfur atom.

(19) A compound or its salt of the above (18), wherein the 5-membered monocyclic group is a pyrazolyl group, an oxazolyl group, a thiazolyl group, an oxydiazolyl group, a thiadiazolyl group or a triazolyl group.

(20) A compound or its salt of the above (16), wherein the heterocyclic group moiety is a 6-membered monocyclic group containing 2 to 3 hetero atoms selected from the group consisting of a nitrogen atom, an oxygen atom and a sulfur atom.

(21) A compound or its salt of the above (20), wherein the 6-membered monocyclic group is:

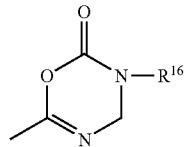

(wherein R is an alkyl group).

(22) A compound or its salt of the above (21), wherein $R^{16}$ is a methyl group or an isopropyl group.

In the present invention, a compound of the formula (I) or its salt is used in combination with other pesticides, examples of which include insecticides, fungicides, microbial agricultural chemicals such as B.T. and insect viruses, but it is preferable to use insecticides and/or fungicides, and it is more preferable to use insecticides. Preferable examples of insecticides usable as an effective component for a pesticidal composition of the present invention are illustrated below.

(A) Organophosphorus Compounds
(A-1) Profenofos
(A-2) Dichlorvos
(A-3) Fenamiphos
(A-4) Fenitrothion
(A-5) EPN
(A-6) Diazinon
(A-7) Chlorpyrifos
(A-8) Acephate
(A-9) Prothiofos
(A-10) Fosthiazate
(A-11) Cadusafos
(A-12) Dislufoton
(A-13) Isoxathion
(A-14) Isofenphos
(A-15) Ethion (I)
(A-16) Etrimfos
(A-17) Quinalphos
(A-18) Dimethylvinphos
(A-19) Dimethoate
(A-20) Sulprofos
(A-21) Thiometon
(A-22) Vamidothion
(A-23) Pyraclofos
(A-24) Pyridaphenthion
(A-25) Pirimiphos-methyl
(A-26) Propaphos
(A-27) Phosalone
(A-28) Formothion
(A-29) Malathion
(A-30) Tetrachlovinphos
(A-31) Chlorfenvinphos
(A-32) Cyanophos
(A-33) Trichlorfon
(A-34) Methidathion
(A-35) Phenthoate
(A-36) Dimethylethylsulfilisopropyl thiophosphate (common name: ESP)
(A-37) Azinphos-methyl
(A-38) Fenthion
(A-39) Heptenophos
(A-40) Methamidphos
(A-41) Paration (B) Carbamate Compounds
(B-1) Carbaryl
(B-2) Propoxur
(B-3) Aldicarb
(B-4) Carbofuran
(B-5) Thiodicarb
(B-6) Methomyl
(B-7) Oxamyl
(B-8) Ethiofencarb
(B-9) Pirimicarb
(B-10) Fenobucarb
(B-11) Carbosulfan (B-12) Benfuracarb
(B-13) Bendiocarb
(B-14) Furathiocab
(B-15) Isoprocarb
(B-16) Metolcarb
(B-17) Xylylcarb
(B-18) 3,5-Xylylmethyl carbamate (common name: XMC)

(C) Pyrethroid Compounds
(C-1) Fenvalerate
(C-2) Permethrin
(C-3) Cypermethrin
(C-4) Deltamethrin
(C-5) Cyhalothrin
(C-6) Tefluthrin
(C-7) Ethofenprox
(C-8) Cyfluthrin
(C-9) Fenpropathrin
(C-10) Flucythrinate
(C-11) Fluvalinate
(C-12) Cycloprothrin
(C-13) Lambda-Cyhalothrin
(C-14) Pyrethrins
(C-15) Esfenvalerate
(C-16) Tetramethrin
(C-17) Resmethrin
(C-18) Protrifenbute
(C-19) Bifenthrin
(C-20) S-Cyano(3-phenoxyphenyl)methyl(±)cis/trans-3-(2,2-dichloroethenyl)-2,2-dimethylcyclopropane carboxylate (D) Neonicotinoid Compounds
(D-1) Imidacloprid
(D-2) Nitenpyram
(D-3) Acetamiprid
(D-4) Thiacloprid
(D-5) Thiamethoxam
(D-6) Clothianidin
(D-7) Dinotefuran
(D-8) 1-(6-chloro-3-pyridylmethyl)-2-(1-nitro-2-allylthioethylidene)imidazolidine (EP437784A)

(E) Benzoylurea Compounds
(E-1) Diflubenzuron
(E-2) Chlorfluazuron
(E-3) Teflubenzuron
(E-4) Flufenoxuron
(E-5) Triflumuron
(E-6) Hexaflumuron
(E-7) Lufenuron
(E-8) Novaluron These compounds work as an IGR agent (insect growth regulating agent).

(F) Nelicetoxin Derivatives
(F-1) Cartap
(F-2) Thiocyclam (G) Hydrazine Compounds
(G-1) Tebufenozide
(G-2) Chlomafenozide
(G-3) Methoxyfenozide
(G-4) N'-t-butyl-N'-3,5-dimethylbenzoyl-N-4,5,6,7-tetrahydrobenzo[b]thiophene-2-carbohydrazide (EP483647A)
(G-5) N'-t-butyl-N'-3,5-dimetylbenzoyl-N-5,6-dihydro-4H-cyclopenta[b]thiophene-2-carbohydrazide (EP483647A)
(G-6) Halofenizide These compounds work as an IGR agent (insect growth regulating agent).

(H) Juvenile Hormone-like Compounds
(H-1) Methoprene
(H-2) Pyriproxyfen
(H-3) Fenoxycarb These benzoylurea type compounds work as an IGR agent (insect growth regulating agent).

(I) Antibiotics
(I-1) Spinosad
(I-2) Emamectin-benzoate
(I-3) Avermectin
(I-4) Milbemycin (J) Pyrrole Compounds
(J-1) Chlorfenapyr (K) Thiadiazine Compounds
(K-1) Buprofezin These compounds work as an IGR agent (insect growth regulating agent).

(L) Silane Compounds
(L-1) Silafluofen (M) Organochlorine Compounds
(M-1) Dicofol
(M-2) Tetradifon
(M-3) Endosulufan (N) Pyrazole Compounds
(N-1) Fenpyroximate
(N-2) Fipronil
(N-3) Tebufenpyrad
(N-4) Ethiprole
(N-5) Tolfenpyrad
(N-6) Acetoprole (O) Organotin Compounds
(O-1) Fenbutatin Oxide In addition, other insecticides usable as a pesticide include a dinitro type compound, an organic sulfur compound, a urea type compound, a triazine type compound, a hydrazone type compound; an IGR agent (insect growth regulating agent) such as Cyromazine; an IGR agent for mites such as Hexythiazox or Etoxazole; Pyridaben, Amitraz, Chlordimeform, Triazamate, Pymetrozine, Pyrimidifen, Indoxacarb, Acequinocyl, 1,3-dichloropropene, Fluacrypyrim, Spirodiclofen, Bifenazate or the like, or *Bacillus thuringienses* or a crystalline protein toxin produced thereby, and the like.

Among the above insecticides, it is preferable to use an IGR agent. As an IGR agent, it is preferable to use at least one member selected from the group consisting of (E) a benzoylurea type compound, (G) a hydrazine type compound, (H) a juvenile hormone-like compound, (K) a thiadiazine type compound, Hexythiazox, Etoxazole and Cyromazine.

Among pesticidal compositions of the present invention comprising a compound of the formula (I) or its salt and an IGR agent as effective components, a pesticidal composition comprising a compound of the formula (I) or its salt and a benzoylurea type compound as effective components achieves a particularly excellent pesticidal effect. As the benzoylurea type compound, it is preferable to use at least one member selected from the group consisting of the compounds illustrated in the above (E-1) to (E-8), but it is more preferable to use at least one compound selected from the group consisting of Diflubenzuron, Chlorfluazuron, Teflubenzuron and Flufenoxuron, and it is most preferable to use Chlorfluazuron and/or Flufenoxuron.

Also, examples of a more preferable form of an insecticide usable as an effective component of a pesticidal composition of the present invention include the following cases.

(1) The insecticide is at least one compound selected from the group consisting of (A) organophosphorus compounds, (B) carbamate compounds, (C) pyrethroid compounds, (D) neonicotinoid compounds, (E) benzoylurea compounds, (F) nelicetoxin derivatives, (G) hydrazine compounds, (H) juvenile hormone-like compounds, (I) antibiotics, (J) pyrrole compounds, (K) thiadiazine compounds, (L) silane compounds, (M) organochlorine compounds, (N) pyrazole compounds, and (O) organotin compounds.

(2) The insecticide is at least one compound of (1) selected from the group consisting of (A) organophosphorus compounds, (B) carbamate compounds, (C) pyrethroid compounds, (D) neonicotinoid compounds, (E) benzoylurea compounds, (F) nelicetoxin derivatives, (G) hydrazine compounds, (H) juvenile hormone-like compounds, (I) antibiotics, (J) pyrrole compounds, (K) thiadiazine compounds, (L) silane compounds and (M) organochlorine compounds.

(3) The insecticide is at least one compound of (2) selected from the group consisting of Dichlorvos, Diazinon, Chlorpyrifos, Acephate, Fosthiazate, Isoxathion, Methidathion, ESP, Methomyl, Ethiofencarb, Pirimicarb, Fenoxycarb, Fenvalerate, Cypermethrin, Deltamethrin, Cyhalothrin, Ethofenprox, Fluvalinate, Acetamiprid, Diflubenzuron, Chlorfluazuron, Teflubenzuron, Flufenoxuron, Cartap, Tebufenozide, Pyriproxyfen, Spinosad, Emamectin-benzoate, Chlorfenapyr, Buprofezin, and Silafluofen.

Further, preferable examples of a fungicide usable as an effective component of a pesticidal composition of the present invention are illustrated below.

(P) Organophosphorus Compounds
(P-1) Fosetyl-Al
(P-2) Tolcofos-Methyl
(P-3) Aluminum ethylhydrogen phosphate
(P-4) Iprobenfos
(P-5) Edifenphos
(P-6) Phosphocarb (Q) Antibiotics
(Q-1) Validamycin
(Q-2) Kasugamycin (R) Organochlorine Compounds
(R-1) Fthalide
(R-2) Chlorothalonil
(R-3) Quintozene
(R-4) Diclomezine (S) Benzanilide Compounds
(S-1) Flutolanil
(S-2) Mepronil
(S-3) Zoxamid (T) Condensed Heterocyclic Compounds Containing a Nitrogen Atom or a Sulfur Atom
(T-1) Tricyclazole
(T-2) Pro. benazole (U) Organotin Compounds
(U-1) Fentin Hydroxide
(U-2) Fentin Acetate Further, examples of an effective component of a fungicide usable as other pesticide include pyrimidinamine compounds such as Mepanipyrim, Pyrimethanil and Cyprodinil;

Azole compounds such as Triadimefon, Bitertanol, Triflumizole, Etaconazole, Propiconazole, Penconazole, Flusilazole, Myclobutanil, Cyproconazole, Terbuconazole, Hexaconazole, Furconazole-cis, Prochloraz, Metconazole, Epoxiconazole, Tetraconazole, Oxpoconazole and Sipconazole;

Quinoxaline compounds such as Quinomethionate;
Dithiocarbamate compounds such as Maneb, Zineb, Mancozeb, polycarbamate and Propineb;
Imidazole compounds such as Benomyl, Thiophanate-Methyl, Carbendazim and Cyazofamid;
Pyridinamine compounds such as Fluazinam;
Cyanoacetamide compounds such as Cymoxanil;
Phenylamide compounds such as Metalaxyl, Oxadixyl, Ofurace, Benalaxyl, Furalaxyl and Cyprofuram;
Sulfenic acid compounds such as Dichlofluanid;
Copper compounds such as Cupric hydroxide and Oxine Copper;
Isoxazole compounds such as Hydroxyisoxazole;
N-halogenothioalkyl compounds such as Captan, Captafol and Folpet;
Dicarboxyimide compounds such as Procymidone, Iprodion and Vinclozolin;
Piperazine compounds such as Triforine;
Pyridine compounds such as Pyrifenox;
Carbinol compounds such as Fenarimol and Flutriafol;
Piperidine compounds such as Fenpropidine;
Morpholine compounds such as Fenpropimorph;
Urea compounds such as Pencycuron;
Cinnamic acid compounds such as Dimethomorph;
Phenylcarbamate compounds such as Diethofencarb;
Cyanopyrrole compounds such as Fludioxonil and Fenpiclonil;
Strobilurin compounds such as Azoxystrobin, Kresoxim-Methyl, Metominofen, Trifloxystrobin and Picoxystrobin; oxazolidinone compounds such as Famoxadone, thiazolecarboxyamide compounds such as Ethaboxam;
Silylamide compounds such as Silthiopham; amino acid amide carbamate compounds such as Iprovalicarb; imidazolidine compounds such as Fenamidone; Hydroxyanilide compounds such as Fenhexamide; Benzenesulfonamide compounds such as Flusulfamid;
Anthraquinone compounds; crotonic acid compounds; Isoprothiolane, Pyroquilon, Quinoxyfen, Propamocarb Hydrochloride, Spiroxamine, Chloropicrin, Dazomet, Metam-sodium, and the like.

Examples of a more preferable form of a fungicide usable as an effective component of a pesticidal composition of the present invention include the following cases.

(1) The fungicide is at least one compound selected from the group consisting of (P) organophosphorus compounds, (O) antibiotics, (R) organochlorine compounds, (S) benzanilide compounds, (T) condensed heterocyclic compounds containing a nitrogen atom or a sulfur atom, and (U) organotin compounds.

(2) The fungicide is at least one compound of (1) selected from the group consisting of Validamycin, Kasugamycin, Fthalide, Dichlomezine, Flutolanil, Tricyclazole and Pro. benazole.

In the pesticidal composition of the present invention, a mixing ratio of at least one of compounds of the formula (I) or their salts and at least one active ingredient of other pesticides is from 1:100 to 100:1, preferably from 1:50 to 50:1.

The pesticidal composition of the present invention may be formulated together with agricultural adjuvants into various forms such as emulsifiable concentrates, dusts, granules, wettable powders, water dispersible granules, suspension concentrates, soluble concentrates, aerosols or pastes, and the like, in the same manner as in a case of conventional agricultural chemicals. Such formulations are usually composed of 0.001 to 99 parts by weight, preferably 0.01 to 95 parts by weight, more preferably 0.01 to 80 parts by weight of an active ingredient and 1 to 99.999 parts by weight, preferably 5 to 99.99 parts by weight, more preferably 20 to 99.99 parts by weight of agricultural adjuvants. When such formulations are to be actually used, they may be used as they are or after being diluted with suitable diluents such as water to a predetermined concentration.

As the agricultural adjuvants, there may be mentioned carriers, emulsifiers, suspending agents, dispersants, extenders, penetrating agents, wetting agents, thickeners, defoaming agents, stabilizers or antifreezing agents. They may be added as the case requires. The carriers may be classified into solid carriers and liquid carriers. As the solid carriers, there may be mentioned powders of animal and plant origin, such as starch, activated carbon, soybean flour, wheat flour, wood powder, fish powder or powdered milk; or mineral powders such as talc, kaolin, bentonite, calcium carbonate, zeolite, diatomaceous earth, white carbon, clay or alumina, sulfur powder, anhydrous sodium sulfate, and the like. As the liquid carriers, there may be mentioned water; alcohols such as methyl alcohol or ethylene glycol; ketones such as acetone, methyl ethyl ketone or N-methyl-2-pyrrolidone; ethers such as dioxane or tetrahydrofuran; aliphatic hydrocarbons such as kerosine, gas oil or the like; aromatic hydrocarbons such as xylene, trimethylbenzene, tetramethylbenzene, cyclohexane or solvent naphtha; halogenated hydrocarbons such as chloroform or chlorobenzene; acid amides such as dimethylformamide; esters such as ethyl acetate or glycerine ester of a fatty acid; nitrites such as acetonitrile; sulfur-containing compounds such as dimethyl sulfoxide; vegetable oils such as soybean oil or corn oil; and the like.

The pesticidal composition of the present invention may be prepared by mixing respective effective components and then formulating the resultant mixture, or may be prepared by formulating respective effective components and then mixing the resultant formulations.

The pesticidal composition of the present invention achieves pesticidal effects against various noxious animals including anthropods such as agriculturally noxious insects, mites and the like; nematodes; and soil insects; or various diseases.

Thus, the pesticidal composition of the present invention is useful as pesticides, for example, insecticides, miticides, nematicides, soil pesticides and fungicides. For instance, it is effective against plant parasitic mites such as two-spotted spider mite (*Tetranychus urticae*), carmine spider mite (*Tetranychus cinnabarinus*), citrus red mite (*Panonychus citri*) or bulb mite (*Rhizoglyphus echinopus*); aphids such as green peach aphid (*Myzus persicae*) or cotton aphid (*Aphis gossypii*); agricultural insect pests such as diamondback moth (*Plutella xylostella*), cabbage armyworm (*Mamestra brassicae*), common cutworm (*Spodoptera litura*), colorado potato beetle (*Leptinotarsa decemlineata*), codling moth (*Laspeyresia pomonella*), bollworm (*Heliothis zea*), tobacco budworm (*Heliothis virescens*), boll weevil (*Anthonomus grandis*), gypsy moth (*Lymantria dispar*), cucurbit leaf beetle (*Aulacophora femoralis*), planthoppers, leafhoppers, scales, bugs, whiteflies, thrips, grasshoppers, anthomyiid flies, scarabs, black cutworm (*Agrotis ipsilon*), cutworm (*Agrotis segetum*) or ants; hygienic insect pests such as cockroaches or housefly (*Musca domestica*); stored grain insects pests such as angoumois grain moth (*Sitotroga cerealella*), azuki bean weevil (*Callosobruchus chinensis*), confused flour beetle (*Tribolium confusum*) or mealworms; and anthropods including household goods insect pests such as casemaking clothes moth (*Tinea pellionella*), black carpet beetle (*Anthrenus scrophularidae*) or subterranean termites; and it is also effective against plant parasitic nematodes such as root-knot nematodes, cyst nematodes, root-lesion nematodes, rice white-tip nematode (*Aphelenchoides besseyi*), strawberry bud nematode (*Nothotylenchus acris*) or pine wood nematode (*Bursaphelenchus lignicolus*). Furthermore, it is effective also against the soil pests. Here, the soil pests include gastropods such as slugs or snails, or isopods such as pillbugs or sowbugs. Further, it is effective against insect pests having acquired resistance to organophosphorus, carbamate and/or synthetic pyrethroid insecticides. Moreover, the composition of the present invention has excellent systemic properties, and by the application of the composition of the present invention to soil treatment, not only soil noxious insects, plant parasitic noxious mites, noxious nematodes, noxious gastropods and noxious isopods in soil but also foliage pests can be controlled.

The pesticidal composition of the present invention is applied in an active ingredient concentration of a compound of the formula (I) or its salt of from 1 to 100,000 ppm, preferably from 1 to 50,000 ppm, more preferably from 10 to 20,000 ppm, and in an active ingredient concentration of other pesticide of from 1 to 100,000 ppm, preferably from 1 to 50,000 ppm, more preferably from 10 to 20,000 ppm. The active ingredient concentration may optionally be changed depending upon the formulation, the manner, purpose, timing or place of the application and the condition of the insect pests. For instance, aquatic noxious insects can be controlled by applying a formulation having the above-mentioned concentration to the site of the outbreak, and thus, the concentration of the active ingredient in water is less than the above-mentioned range.

The amount of the application of the active ingredient per unit surface area is usually from about 1 to 50,000 g, preferably from 10 to 10,000 g, per hectare as an active ingredient of a compound of the formula (I) or its salt, and from about 1 to 50,000, preferably from 10 to 10,000 g, per hectare as an active ingredient of other pesticide. However, in a certain special case, the amount of the application may be outside the above range. Various formulations containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a food containing the above active ingredient and to control the outbreak or growth of pests, particularly insects pests, with their excrements. Furthermore, the active ingredient may also be applied by a so-called ultra low-volume application method. In this method, the composition may be composed of 100% of the active ingredient.

EXAMPLES

Now, the present invention will be described with reference to Formulation Examples of a pesticidal composition. However, it should be understood that the present invention is by no means restricted by these specific Examples in respect of kinds of an effective component compound and an agricultural chemical aid, blending ratios, formulations and the like.

Formulation Example 1

| | | |
|---|---|---|
| (A) | Compound No. 1 | 20 parts by weight |
| (B) | Compound D-3 | 10 parts by weight |
| (C) | Kaolin | 42 parts by weight |
| (D) | Sodium ligninsulfonate | 8 parts by weight |
| (E) | White carbon | 20 parts by weight |

The above components are uniformly mixed to obtain a wettable powder.

Formulation Example 2

| | | |
|---|---|---|
| (A) | Compound No. 1 | 3 parts by weight |
| (B) | Compound L-1 | 1.5 parts by weight |
| (C) | Talc | 95.5 parts by weight |

The above components are uniformly mixed to obtain a dust.

Formulation Example 3

| | | |
|---|---|---|
| (A) | Compound No. 1 | 10 parts by weight |
| (B) | Compound B-8 | 50 parts by weight |
| (C) | N-methyl-2-pyrrolidone | 10 parts by weight |
| (D) | Polyoxyethylenealkylphenyl ether | 10 parts by weight |
| (E) | Xylene | 20 parts by weight |

The above components are uniformly mixed and dissolved to obtain an emulsifiable concentrate.

Formulation Example 4

| | | |
|---|---|---|
| (A) | Kaolin | 83 parts by weight |
| (B) | Sodium ligninsulfonate | 2 parts by weight |
| (C) | Polyoxyethylenealkylaryl sulfate | 5 parts by weight |
| (D) | Fine silica powder | 10 parts by weight |

A mixture of the above components, Compound No. 1 and Compound D-3 are mixed in a weight ratio of 7:2:1 to obtain a wettable powder.

Formulation Example 5

| | | |
|---|---|---|
| (A) | Compound No. 1 | 20 parts by weight |
| (B) | Compound E-2 | 10 parts by weight |
| (C) | Oxylated polyalkylphenyl phosphate-triethanolamine | 2 parts by weight |
| (D) | Silicone | 0.2 part by weight |
| (E) | Xanthan gum | 0.1 part by weight |
| (F) | Ethylene glycol | 5 parts by weight |
| (G) | Water | 62.7 parts by weight |

The above components are uniformly mixed and pulverized to obtain an aqueous suspension.

Formulation Example 6

| | | |
|---|---|---|
| (A) | Compound No. 1 | 25 parts by weight |
| (B) | Compound B-9 | 50 parts by weight |
| (C) | Sodium polycarboxylate | 13.5 parts by weight |
| (D) | Anhydrous sodium sulfate | 10 parts by weight |
| (E) | Dextrin | 0.5 part by weight |
| (F) | Sodium alkylsulfonate | 1 part by weight |

The above components are placed in a high speed mixing granulator, and 20% of water is added thereto, and the resultant mixture is granulated and dried to obtain wettable granules.

Formulation Example 7

| | | |
|---|---|---|
| (A) | Compound No. 1 | 5 parts by weight |
| (B) | Compound A-8 | 5 parts by weight |
| (C) | Bentonite | 33 parts by weight |
| (D) | Kaolin | 52 parts by weight |
| (E) | Sodium ligninsulfonate | 5 parts by weight |

Water is added to the above components in such an appropriate amount as required for granulation, and the resultant mixture was granulated to obtain granules.

Formulation Example 8

| | | |
|---|---|---|
| (A) | Compound No. 1 | 2 parts by weight |
| (B) | Compound C-3 | 0.5 part by weight |
| (C) | N-methyl-2-pyrrolidone | 2.5 parts by weight |
| (D) | Soybean oil | 95.0 parts by weight |

The above components are uniformly mixed and dissolved to obtain an ultra low volume formulation.

Formulation Example 9

| | | |
|---|---|---|
| (A) | Compound No. 1 | 10 parts by weight |
| (B) | Compound A-34 | 10 parts by weight |
| (C) | N-methyl-2-pyrrolidone | 5 parts by weight |
| (D) | Polyoxyethylenealkylaryl ether | 10 parts by weight |
| (E) | Xylene | 65 parts by weight |

The above components are uniformly mixed to obtain an emulsifiable concentrate.

Formulation Example 10

| | | |
|---|---|---|
| (A) | Compound No. 1 | 10 parts by weight |
| (B) | Compound G-1 | 10 parts by weight |
| (C) | Corn oil | 67 parts by weight |

-continued

|     |                                      |                 |
| --- | ------------------------------------ | --------------- |
| (D) | Polyoxyethylene hardened castor oil  | 12 parts by weight |
| (E) | Organic bentonite                    | 1 part by weight |

The above components are uniformly mixed and pulverized to obtain a suspension.

Formulation Example 11

|     |                  |                   |
| --- | ---------------- | ----------------- |
| (A) | Compound No. 1   | 3 parts by weight |
| (B) | Compound S-1     | 2 parts by weight |
| (C) | Talc             | 95 parts by weight |

The above components are uniformly mixed to obtain a dust.

Formulation Example 12

|     |                  |                   |
| --- | ---------------- | ----------------- |
| (A) | Compound No. 1   | 3 parts by weight |
| (B) | Compound T-1     | 1 part by weight  |
| (C) | Clay             | 96 parts by weight |

The above components are uniformly mixed to obtain a dust.

Formulation Example 13

|     |                  |                     |
| --- | ---------------- | ------------------- |
| (A) | Compound No. 1   | 3 parts by weight   |
| (B) | Compound L-1     | 0.5 part by weight  |
| (C) | Talc             | 96.5 parts by weight |

The above components are uniformly mixed to obtain a dust.

Formulation Example 14

|     |                  |                   |
| --- | ---------------- | ----------------- |
| (A) | Compound No. 1   | 3 parts by weight |
| (B) | Compound R-1     | 2 parts by weight |
| (C) | Clay             | 95 parts by weight |

The above components are uniformly mixed to obtain a dust.

Formulation Example 15

|     |                  |                     |
| --- | ---------------- | ------------------- |
| (A) | Compound No. 1   | 3 parts by weight   |
| (B) | Compound Q-1     | 0.3 part by weight  |
| (C) | Talc             | 96.7 parts by weight |

The above components are uniformly mixed to obtain a dust.

Test Example 1

Insecticidal Test (1) of *Thrips palmi*

An agrochemical liquid diluted to a predetermined concentration was applied by a spray gun to a 10 to 12-foliate eggplant having *Thrips palmi* parasitic thereon in a pot so as to make the eggplant fully wet with the agrochemical liquid, and the pot was placed in a greenhouse. The numbers of the parasitic insects were counted before treatment and three days after the treatment, and a Percent Control was calculated in accordance with the following formula, and the results are shown in the following Table 1.

Percent Control=$100-((Ta \times Cb)/(Tb \times Ca) \times 100)$

Ta: Number of insects per treated plants after treatment
Tb: Number of insects per treated plants before treatment
Ca: Number of insects per untreated plants after treatment
Cb: Number of insects per untreated plants before treatment Also, a theoretical value of the Percent Control was calculated in accordance with the following Colby formula.

When value of the Percent Control is higher than the theoretical value (%) (in accordance with the Colby formula), it is considered that the pesticidal composition of the present invention achieves a synergistic pesticidal effect. The theoretical values of the Percent Control calculated in accordance with the Colby formula are shown in parentheses in the following Table 1.

Theoretical value of the Percent Control=$100-(X \times Y)/100$

X: $100-$(Percent Control in case of treating with Compound No. 1 only)
Y: $100-$(Percent Control in case of treating with Flufenoxuron only)

TABLE 1

| Flufenoxuron | Compound No. 1 | | |
| --- | --- | --- | --- |
| (E-4) | 0 ppm | 25 ppm | 50 ppm |
| 0 ppm | 0 | 43 | 24 |
| 12.5 ppm | 70 | 73.7 | 84 (77) |
| 25 ppm | 67 | 85 (81) | 86 (75) |

Number of replications: 2

Test Example 2

Insecticidal Test on (2) of *Thrips Palmi*

An agrochemical liquid diluted to a predetermined concentration was applied by a spray gun to a 10 to 12 foliate eggplant having *Thrips palmi* parasitic thereon in a pot so as to make the eggplant fully wet with the agrochemical liquid, and the pot was placed in a greenhouse.

The numbers of the parasitic insects were counted before treatment and 7 days after the treatment, and a Percent Control was calculated in the same manner as in Test Example 1, and the results are shown in the following Table 2.

Also, a theoretical mortality value (%) was calculated in accordance with the following Colby formula. When value of the Percent Control is higher than the theoretical value of the Percent Control (in accordance with the Colby formula), it is considered that the pesticidal composition of the present invention achieves a synergistic pesticidal effect. The theoretical values of the Percent Control calculated in accordance with the Colby formula are shown in parentheses in the following Table 2.

Theoretical value of the Percent Control=100−($X \times Y$)/100

X: 100−(Percent Control in case of treating with Compound No. 1 only)
Y: 100−(Percent Control in case of treating with Chlorfluazuron only)

TABLE 2

| Chlorfluazuron | Compound No. 1 | | |
|---|---|---|---|
| (E-2) | 0 ppm | 25 ppm | 50 ppm |
| 0 ppm | 0 | 48 | 55 |
| 12.5 ppm | 55 | 77 (76) | 74 |
| 25 ppm | 52 | 92 (75) | 85 (78) |

Number of replications: 2

Test Example 3

Insecticidal Test of Western Flower Thrips *Frankliniella occidentalis*

An agrochemical liquid diluted to a predetermined concentration was applied by a spray gun to a 10 to 12 foliate eggplant having Western Flower Thrips *Frankliniella occidentalis* parasitic thereon in a pot so as to make the eggplant fully wet with the agrochemical liquid, and the pot was placed in a greenhouse. The numbers of the parasitic insects were counted before treatment and 2 days after the treatment, and a Percent Control was calculated in the same manner as in Test Example 1. The results are shown in the following Table 3.

Also, a theoretical value of the Percent Control was calculated in accordance with the Colby formula in the same manner as in Test Example 1, and the results are shown in parenthesis in the following Table 3.

TABLE 3

| | Concentration (ppm) | Mortality (%) |
|---|---|---|
| Compound No. 1 + Flufenoxuron (E-4) | 50 + 25 | 93 (90) |
| Compound No. 1 | 50 | 86 |
| Flufenoxuron (E-4) | 25 | 31 |

Number of replications: 2

Test Example 4

Insecticidal Test of *Thrips palmi* (Test in a Vinyl House)

An agrochemical liquid diluted to a predetermined concentration was applied by a shoulder sprayer on a 6 to 8 foliate eggplant having *Thrips palmi* parasitic thereon in an amount of 100 l per 10 are. The numbers of the parasitic insects were counted before treatment and 12 days-after the treatment, and a Percent Control was calculated in the same manner as in Test Example 1, and the results are shown in the following Table 4.

Also, a theoretical value of the Percent Control calculated in accordance with the Colby formula in the same manner as in Test Example 2 are shown in parenthesis in the following Table 4.

TABLE 4

| | Concentration (ppm) | Mortality |
|---|---|---|
| Compound No. 1 + Chlorfluozuron (E-2) | 50 + 25 | 91 (79) |
| Compound No. 1 | 50 | 51 |
| Chlorfluazuron (E-2) | 25 | 58 |

Number of replications: 2, 5 plants/plot

The pesticidal composition of the present invention achieves a stable high pesticidal effect, and noxious insects and other organisms can be killed by this composition.

The invention claimed is:

1. A pesticidal composition comprising a synergistically pesticidally effective amount of N-cyanomethyl-4-trifluoromethyl-3-pyridine-carboxyamide or its salt; and
    at least one additional insecticide selected from the group consisting of Carbofuran, Carbosulfan, Cypermethrin, Acetamiprid, Chlorfluazuron, Flufenoxuron, Pyriproxyfen, Avermectin, Buprofezin, and Fipronil.

2. The pesticidal composition according to claim 1, wherein the additional insecticide is at least one member selected from the group consisting of Cypermethrin, Acetamiprid, Chlorfluazuron, Flufenoxuron, Pyriproxyfen, and Buprofezin.

3. The pesticidal composition according to claim 1, wherein the additional insecticide is an IGR agent.

4. The pesticidal composition according to claim 3, wherein the IGR agent is a benzoylurea type compound.

5. The pesticidal composition according to claim 4, wherein the benzoylurea type compound is Chlorfluazuron and/or Flufenoxuron.

* * * * *